United States Patent
DeMello

(10) Patent No.: US 8,961,435 B2
(45) Date of Patent: Feb. 24, 2015

(54) COAXIAL GUIDEWIRE FOR SMALL VESSEL ACCESS

(75) Inventor: Richard M. DeMello, Stow, MA (US)

(73) Assignee: Radius Medical LLC, Hudson, MA (US)

( * ) Notice: Subject to any disclaimer, the term of this patent is extended or adjusted under 35 U.S.C. 154(b) by 0 days.

(21) Appl. No.: 13/586,236

(22) Filed: Aug. 15, 2012

(65) Prior Publication Data

US 2013/0046203 A1 Feb. 21, 2013

Related U.S. Application Data

(60) Provisional application No. 61/524,943, filed on Aug. 18, 2011.

(51) Int. Cl.
*A61M 25/09* (2006.01)

(52) U.S. Cl.
CPC ..... *A61M 25/09* (2013.01); *A61M 2025/09083* (2013.01)
USPC ...................... 600/585; 604/164.13

(58) Field of Classification Search
CPC .............. A61M 25/09025; A61M 2025/09083
USPC ................. 600/434, 585, 164.13; 604/164.13
See application file for complete search history.

(56) References Cited

U.S. PATENT DOCUMENTS

| | | | | |
|---|---|---|---|---|
| 4,676,249 A | * | 6/1987 | Arenas et al. | 600/434 |
| 4,779,628 A | * | 10/1988 | Machek | 600/585 |
| 4,846,193 A | * | 7/1989 | Tremulis et al. | 600/585 |
| 4,884,579 A | * | 12/1989 | Engelson | 600/585 |
| 4,895,168 A | * | 1/1990 | Machek | 600/585 |
| 5,551,444 A | | 9/1996 | Finlayson | |
| 5,762,615 A | * | 6/1998 | Weier | 600/585 |
| 5,885,227 A | | 3/1999 | Finlayson | |
| 5,954,672 A | * | 9/1999 | Schwager | 600/585 |
| 6,132,389 A | * | 10/2000 | Cornish et al. | 600/585 |
| 6,544,197 B2 | | 4/2003 | DeMello | |
| 2003/0139689 A1 | * | 7/2003 | Shturman et al. | 600/585 |
| 2003/0163064 A1 | * | 8/2003 | Vrba et al. | 600/585 |
| 2004/0193073 A1 | | 9/2004 | DeMello et al. | |
| 2007/0021731 A1 | * | 1/2007 | Garibaldi et al. | 604/510 |
| 2008/0281228 A1 | * | 11/2008 | Parodi et al. | 600/585 |

* cited by examiner

*Primary Examiner* — Max Hindenburg
*Assistant Examiner* — John Pani
(74) *Attorney, Agent, or Firm* — Cesari and McKenna, LLP; Patricia A. Sheehan

(57) ABSTRACT

A coaxial guidewire for use in accessing smaller vessels within a patient's body, consists of an inner core wire and an outer hollow wire. The distal end of the inner core wire tapers and supports a spring coil. The core wire, including the spring coil, fits within a 25-gauge needle that is used to locate an artery of the patient. When the needle is removed over the inner core wire, the outer hollow wire, having a distal end that tapers to the outer diameter of the spring coil, fits over the inner wire and is advanced until the distal end of the outer wire meets the spring coil of the core wire. A dilator and introducer sheath combination may then be fed over the assembled coaxial guidewire. When the distal end of the sheath is in the desired position, the dilator and the coaxial guidewire are removed.

19 Claims, 4 Drawing Sheets

US 8,961,435 B2

COAXIAL GUIDEWIRE FOR SMALL VESSEL ACCESS

CROSS-REFERENCE TO RELATED APPLICATIONS

This application claims the benefit of U.S. Provisional Patent Application Ser. No. 61/524,943, which was filed Aug. 18, 2011, by Richard DeMello for a "Coaxial Guidewire For Small Vessel Access" and is hereby incorporated by reference.

BACKGROUND OF THE INVENTION

1. Field of the Invention

The invention relates generally to guidewires, and more particularly, to guidewires for use in accessing small arterial or venous vessels within a patient's body such as the adult radial artery or the arteries of a pediatric patient.

2. Background Information

Recent studies have shown that there are benefits associated with utilizing the radial artery for angiography and other intravascular medical procedures that have typically been performed through the femoral artery. See, for example, Duke Clinical Research Institute article entitled RIVAL Trial Shows Significant Benefits With Radial Approach of Angiography Report dated Apr. 4, 2011. The known procedures for accessing an artery to conduct a medical procedure such as angiography, involves placement of a valved introducer sheath into the artery. The introducer sheath acts as a conduit to pass various medical devices into and out of the artery, while preventing significant blood loss. The introducer sheaths for use with the radial artery approach, which are typically referred to as "micro access" or "micro puncture" sets, accept 5 French (0.066 inch outer diameter) or 6 French (0.079 inch outer diameter) catheters and devices.

The known procedure to place the introducer sheaths into the artery begin with the insertion of a 21-gauge (0.032 inch outer diameter) needle into the artery. A 0.018 inch diameter guidewire is next passed through the needle and into the artery so that the distal portion of the guidewire resides at a desired location within the artery and the proximal portion of the guidewire extends out of the patient. The needle is then withdrawn from the patient over the back of the guidewire, leaving the guidewire extending through the skin and into the artery. Next, a vessel dilator, which is a hollow plastic tube having an outer diameter that is sized to closely fit within the introducer sheath's inner diameter, is placed into the introducer sheath so that the distal end of the dilator extends slightly beyond the distal end of the sheath. The extended distal portion of the dilator has an inner diameter capable of passing over the 0.018 inch guidewire and is smoothly tapered to an outer diameter that is slightly larger than the diameter of the guidewire. The sheath/dilator combination is advanced over the proximal end of the 0.018 inch guidewire and the tapered dilator end is used to gradually enlarge the vessel access site to accommodate the introducer sheath. Once the distal end of the sheath is in place within the vessel, the dilator and the 0.018 inch guidewire are removed from the patient through the inside of the sheath, leaving the valved introducer sheath as an access point for inserting other medical devices.

The 0.018 guidewire is used to support the dilator/sheath combination as that combination is advanced. The amount of force required to allow the dilator/sheath combination to advance tends to bend and kink guidewires of smaller diameters, which prevents the proper insertion of the introducer sheath. The use of a 21-gauge needle is required to accommodate the 0.018 inch guidewire and allow the needle to be withdrawn.

While the insertion procedure works well for access to the relatively large femoral artery, the size of the needle makes it difficult to locate the smaller radial artery. The procedure also makes it difficult to locate either artery in pediatric patients. The difficulty in locating the smaller vessels with the large needles results in the patients being subjected to painful needle sticks followed often by painful movement of the needles.

SUMMARY OF THE INVENTION

A coaxial guidewire for use in accessing smaller vessels within a patient's body, such as, for example, arteries in a pediatric patient or the adult radial artery, consists of an inner core wire and an outer hollow wire that has an inner diameter sized to fit over the inner core wire. The inner core wire has an outer diameter of 0.010 inches and tapers at a distal end. The distal end of the inner core wire supports a spring coil with an outer diameter of 0.014 inches. The core wire, including the spring coil, fits within a 25-gauge needle that is used to locate the artery. When the needle is removed over the inner core wire, the outer hollow wire, which has an outer diameter of 0.018 inches for a majority of its length and a distal end that tapers to the outer diameter of the spring coil, fits over the inner wire and is advanced until the distal end of the outer wire meets the spring coil that is at the distal end of the core wire.

Once the outer wire is in place over the inner core wire, the dilator and introducer sheath combination are fed over the assembled coaxial guidewire. The coaxial guidewire, which has an outer diameter of 0.018 inches up to a distal end that is 0.014 inches, provides the support necessary to prevent kinking as the dilator and introducer sheath combination are advanced to a desired arterial position over the guidewire. When the distal end of the sheath is in the desired position, the dilator and the coaxial guidewire are removed via the sheath.

The use of the coaxial guidewire to position the introducer sheath in the body allows the use of a 25-gauge needle, which is significantly smaller than the 21-gauge needle required with conventional procedures.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
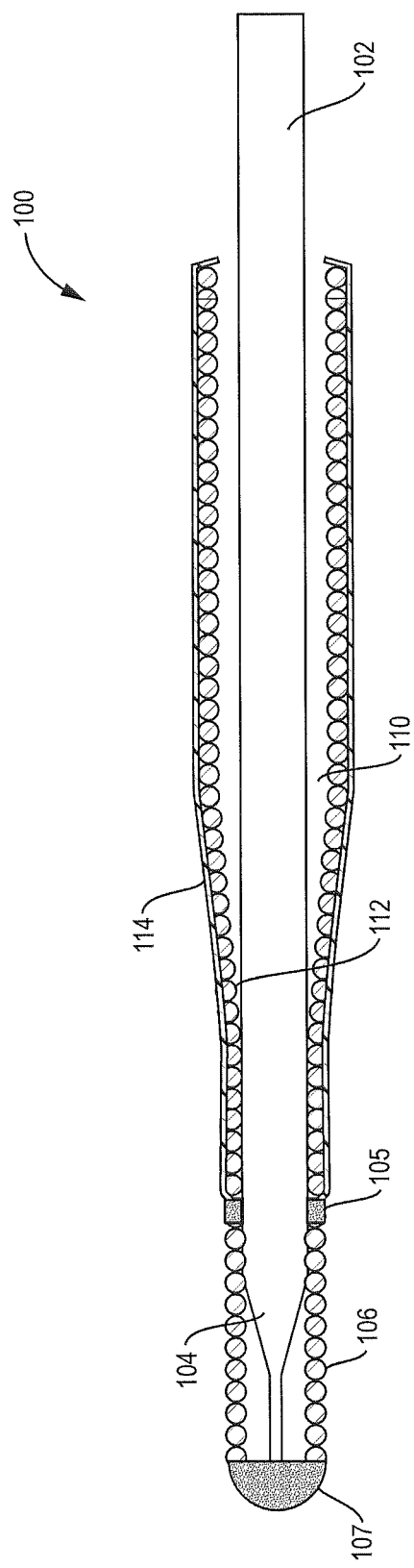
FIG. 1 is an illustration of an assembled coaxial guidewire constructed in accordance with the invention.
Figure 2:
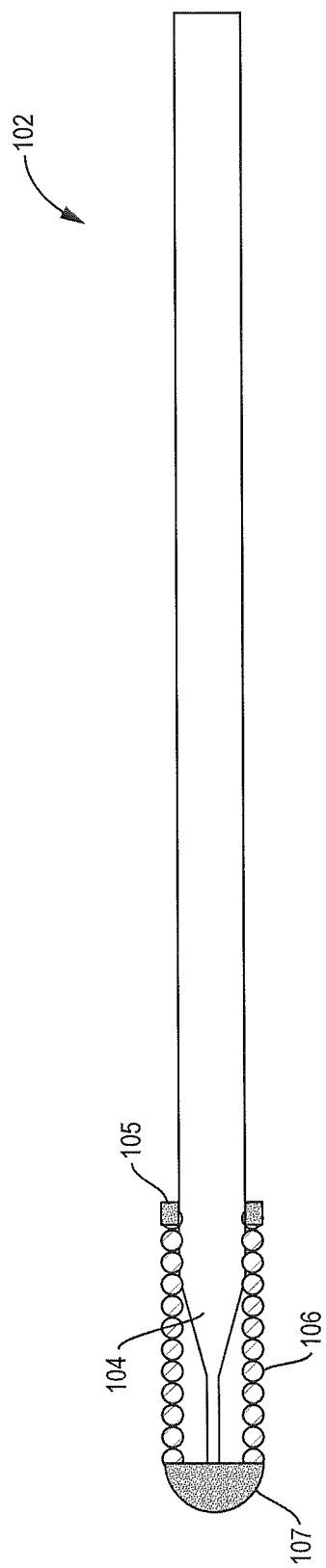
FIG. 2 is a more detailed illustration of a core guidewire included in the assembled coaxial guidewire of FIG. 1.
Figure 3:
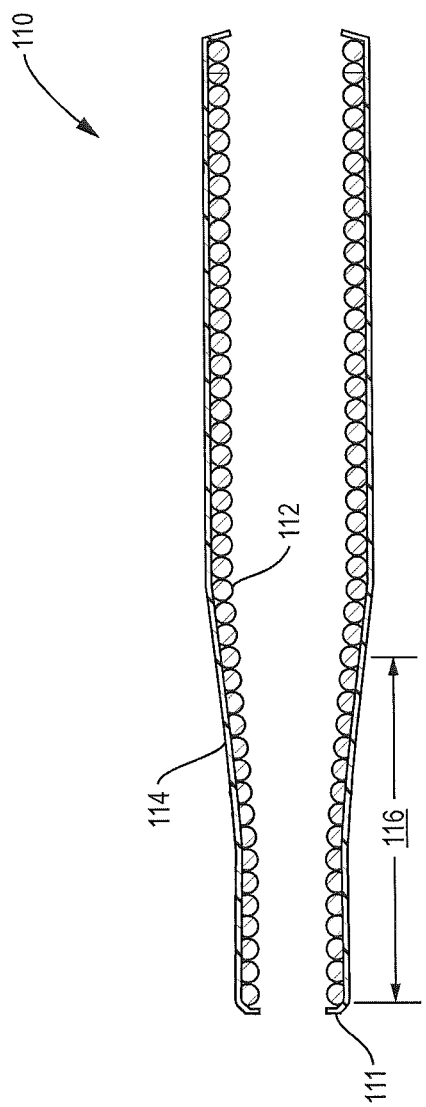
FIG. 3 is a more detailed illustration of an outer guidewire included in the assembled coaxial guidewire of FIG. 1.

Referring to FIGS. 1-3, a coaxial guidewire 100 includes an inner guidewire 102 that consists of an elongated solid stainless steel core wire approximately 60 centimeters in length with an outer diameter (OD) of approximately 0.010 inches. The core wire has a gradually tapered distal end 104 of approximately 4 centimeters that provides increased flexibility. A stainless steel guidewire spring coil 106, having an OD of approximately 0.014 inches and a length of approximately 6 centimeters is affixed over the distal portion of the guidewire and covers the entire tapered portion. The proximal end 105 of the spring coil may be attached to the inner core guidewire by adhesives, welding, brazing or using any other well known techniques or combinations thereof. As shown in the drawings, the core guidewire may include an atraumatic tip 107 attached to the distal end of the spring coil 106.

A hollow outer guidewire 110, which is made from a wound stainless steel spring coil 112 and covered with a polymer sleeve 114, has an inner diameter that is sized to fit over the inner core wire 102. The outer guidewire is approximately 40 cm long and with the sleeve has an OD of approximately 0.018 inches over the majority of its length. A distal end portion 116 of the outer guidewire tapers to the size of the OD of the spring coil 106 that covers the distal end 104 of the inner core guidewire 102. The tapered distal end 116 of the outer guidewire thus tapers to an OD of approximately 0.014 inches. When the outer guidewire is advanced over the inner guidewire core to meet the distal end of the inner guidewire, the assembled device 100 functions essentially as a single guidewire that has a tapered distal end with a 0.14 inch OD and otherwise has a 0.018 inch OD over the majority of the length of the assembled guidewire.

Figure 4:
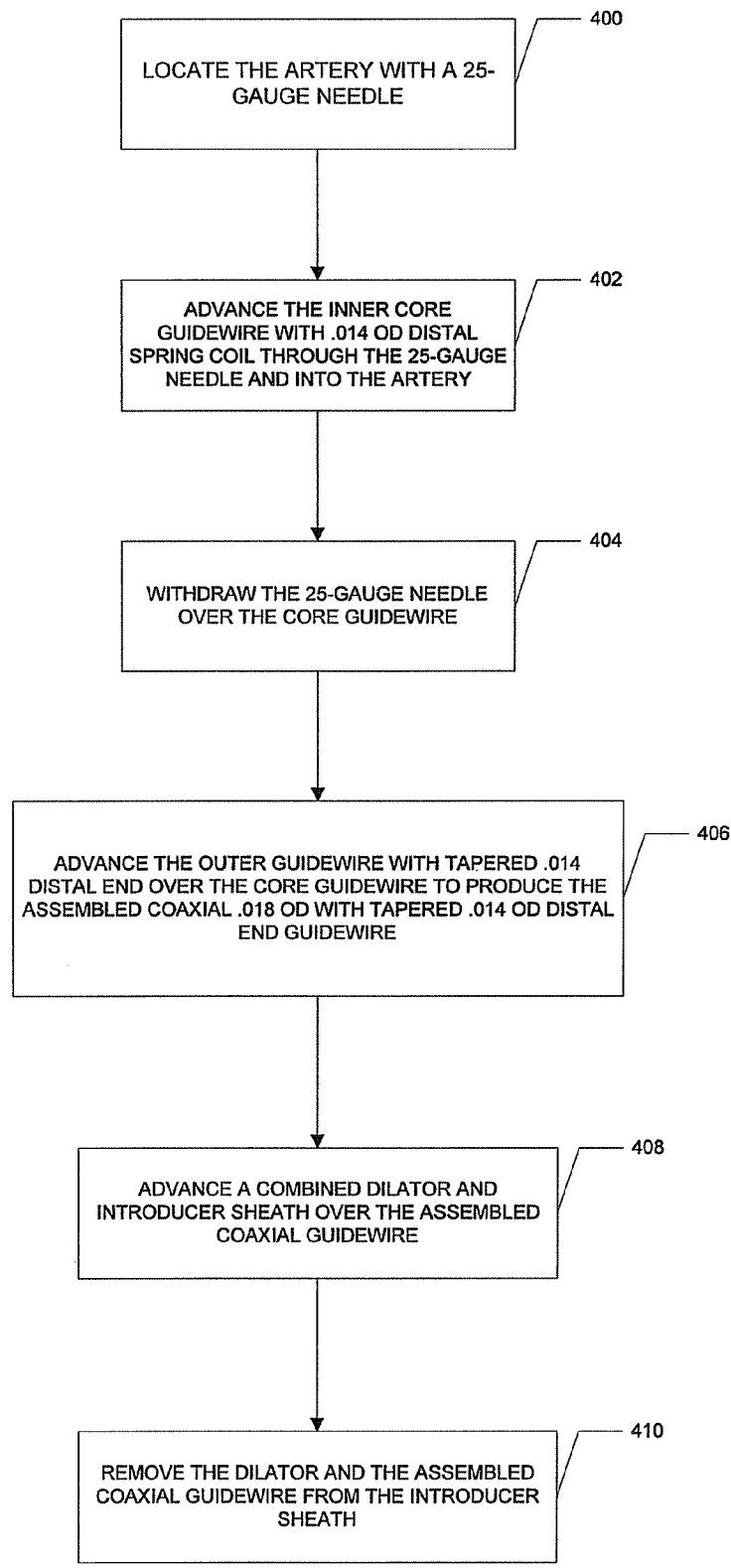
FIG. 4 is a flow chart of the operations of the introduction procedure.

The coaxial guidewire 100 is utilized to insert an introducer into small vessels and operates with a 25-gauge needle (0.020 inch OD), which is significantly smaller in diameter than the 21-gauge needle (0.032 inch OD) required for the conventional introducer sheath insertion procedure. Referring now also FIG. 4, the insertion procedure utilizing the coaxial guidewire 100 starts with the location of the artery with a 25-gauge needle (not shown) (Step 400). Next, the inner core guidewire 102, which has a 0.014 inch OD at the distal end with the spring coil 106 attached, is passed through the 25-gauge needle and advanced into the artery until a distal portion of the guidewire resides within the artery and a proximal portion of the core guidewire extends outside of the patient (Step 402). The needle is then withdrawn from the patient over the back of the 0.014 inch OD core guidewire 102 (Step 404).

The outer guidewire 110 is next fed over the proximal end 107 of the core guidewire 102 and advanced into the vessel until the distal end 111 of the outer guidewire meets the spring coil 106 that covers the tapered distal end 104 of the core guidewire 102, to assemble the coaxial guidewire 100 as depicted in FIG. 1 (Step 406). A dilator (not shown) is fed into an introducer sheath (not shown) in a conventional manner that is well understood by those skilled in the art, and the dilator/sheath combination is then advanced over the coaxial guidewire 100, until a distal portion of the sheath resides at a desired location within the vessel (Step 408). With the distal portion of the sheath in place in the vessel, the dilator and the coaxial guidewire 100 are removed from the body through the sheath (Step 410).

The use of the smaller gauge needle, that is, the 25-gauge needle as opposed to the 21-gauge needle, results in a less painful insertion procedure, and in particular, in reduced pain during the location of the artery using the needle. Further, the assembled coaxial guidewire, which has a 0.018 OD over much of its length and is a combination of a stainless steel core wire and an elongated outer spring coil, is appropriately sized and has sufficient strength and resilience to prevent the coaxial guidewire from bending and kinking as the sheath/dilator combination is advanced over the assembled coaxial guidewire into the artery.

The foregoing description has been directed to a specific embodiment of this invention. It will be apparent, however, that other variations and modifications may be made to the described embodiments, with the attainment of some or all of their advantages. For instance, it is expressly contemplated that the assemblies, systems, and materials described herein may be implemented in various forms. Furthermore, in alternate embodiments, the coaxial guidewire may include additional guidewire components with appropriately sized inner and outer diameters and/or the core guidewire component of the coaxial guidewire may be sized to be utilized with smaller gauge needles. The spring coil 106 covering the distal end of the core guidewire may be longer or shorter, and may but need not be made of radiopaque material. The outer surface of either or both of the inner and outer guidewires may be covered with a lubricious coating, to reduce friction. Either or both of the inner and outer guidewires may be made from kink-resistant material, such as nickel-titanium or cobalt alloys. In addition, either or both of the distal end spring coil and the outer guidewire spring coil may be made from round coiling wire or flat coiling wire. Further, either or both of the distal end and outer guidewire spring coils may be made from nickel titanium or cobalt alloy wire. Accordingly, this description is to be taken only by way of example and not to otherwise limit the scope of the invention.

What is claimed is:

1. A coaxial guidewire utilized to introduce a sheath within a vessel of a human body, the coaxial guidewire comprising:
    an inner guidewire, including a spring coil that is affixed to distal end of a core wire and has a proximal end that is attached to the core wire, the inner guidewire being sized to pass through a needle that is sized to be placed within the vessel of the human body; and
    a hollow outer guidewire having
        a distal end that tapers to an outer diameter of the spring coil that is affixed to the distal end of the inner guidewire, and
        an inner diameter that allows the hollow guidewire to advance over a proximal end of the inner guidewire,
    the hollow outer guidewire being configured to be advanced over a proximal end of the inner guidewire until the distal end meets the spring coil affixed to the distal end of the core wire to assemble the coaxial guidewire, the hollow guidewire and the inner guidewire being capable of sliding relative to each other;
    the core wire being configured to extend proximally to a proximal end of the hollow outer guide wire when the distal end meets the spring coil; and
    the hollow outer guidewire having a distal opening with an inner diameter less than the outer diameter of the spring coil.

2. The coaxial guidewire of claim 1, wherein the needle is a 25-gauge needle.

3. The coaxial guidewire of claim 1, wherein the inner guidewire is configured to an outer diameter of 0.010 inches or less at a proximal end and tapers to the distal end.

4. The coaxial guidewire of claim 1, wherein the spring coil affixed to the inner guidewire distal end has an outer diameter of 0.014 inches or less.

5. The coaxial guidewire of claim 1, wherein the hollow outer guidewire has an outer diameter of 0.018 inches or less at the proximal end and tapers to the distal end.

6. The coaxial guidewire of claim 1, wherein the hollow outer guidewire has an outer diameter at the proximal end of 0.018 inches and an outer diameter of 0.014 inches at the distal end.

7. The coaxial guidewire of claim 1, wherein
    the coaxial guidewire is configured to allow a dilator and the sheath to be fed over the coaxial guidewire, to introduce and position the sheath within the vessel, into which the inner guidewire was introduced by passing through the needle, and allow the dilator to be removed from the vessel with the coaxial guidewire, to leave the sheath within the vessel.

8. The coaxial guidewire of claim 1, wherein the inner guidewire includes an atraumatic tip at the distal end.

9. The coaxial guidewire of claim 1, wherein the hollow outer guidewire is covered with a polymer sleeve.

10. The coaxial guidewire of claim 1, wherein the hollow outer guidewire is a wound stainless steel spring coil.

11. A method to position an introducer sheath in a vessel of a human body, the method comprising:

introducing a distal end of an inner guidewire through a needle that is inserted within the vessel of the human body, wherein the inner guidewire includes a spring coil affixed to the distal end;

withdrawing, over the inner guidewire, the needle from the vessel of the human body;

feeding an outer guidewire over a proximal end of the inner guidewire, wherein the outer guidewire meets the spring coil affixed to the distal end of the inner guidewire to produce a coaxial guidewire that is within the vessel of the human body;

advancing a dilator and sheath combination into the vessel of the human body over the coaxial guidewire; and removing the coaxial guidewire and the dilator from the vessel, thereby leaving the sheath within the vessel of the human body.

12. The method of claim 11, wherein the inner guidewire has an outer diameter of 0.010 inches or less at a proximal end and tapers to the distal end.

13. The method of claim 11, wherein the spring coil has an outer diameter of 0.014 inches or less.

14. The method of claim 11, wherein the needle is a 25-gauge needle.

15. The method of claim 11, wherein the coaxial guidewire has an outer diameter of 0.018 inches or less at the proximal end and tapers at the distal end to an outer diameter of 0.014 inches or less.

16. The method of claim 11, wherein the outer guidewire is covered by a polymer sleeve.

17. The method of claim 11, wherein the outer guidewire is hollow.

18. The method of claim 11, wherein the outer guidewire is a wound stainless steel spring coil.

19. The method of claim 11, wherein the vessel is an artery.

* * * * *

UNITED STATES PATENT AND TRADEMARK OFFICE
CERTIFICATE OF CORRECTION

| | | |
|---|---|---|
| PATENT NO. | : 8,961,435 B2 | Page 1 of 1 |
| APPLICATION NO. | : 13/586236 | |
| DATED | : February 24, 2015 | |
| INVENTOR(S) | : Richard M. DeMello | |

It is certified that error appears in the above-identified patent and that said Letters Patent is hereby corrected as shown below:

In the Claims:

Claim 1, Col. 4, line 43, should read:
guidewire, the hollow outer guidewire and the inner guidewire Claim 7, Col. 5, line 3, should read:
the vessel into which the inner guidewire was intro- Signed and Sealed this
Twenty-third Day of June, 2015

Michelle K. Lee
*Director of the United States Patent and Trademark Office*